(12) United States Patent
Thoe

(10) Patent No.: US 12,161,549 B2
(45) Date of Patent: Dec. 10, 2024

(54) SYSTEMS AND METHODS FOR PROVIDING A GRAPHICAL USER INTERFACE FOR INTRAOCULAR LENS IMPLANTATION PLANNING

(71) Applicant: Alcon Inc., Fribourg (CH)

(72) Inventor: David Thoe, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 1119 days.

(21) Appl. No.: 17/025,543

(22) Filed: Sep. 18, 2020

(65) Prior Publication Data

US 2021/0093446 A1    Apr. 1, 2021

Related U.S. Application Data

(60) Provisional application No. 62/906,754, filed on Sep. 27, 2019.

(51) Int. Cl.
*A61F 2/16*    (2006.01)
*A61B 3/00*    (2006.01)
*A61B 34/10*   (2016.01)

(52) U.S. Cl.
CPC .......... *A61F 2/1618* (2013.01); *A61B 3/0025* (2013.01); *A61B 34/10* (2016.02); *A61F 2/16* (2013.01); *A61B 2034/108* (2016.02); *A61F 2240/002* (2013.01); *A61F 2250/006* (2013.01)

(58) Field of Classification Search
CPC ... A61B 3/0025; A61B 2034/108; A61B 3/10; A61B 3/113; A61B 34/10; A61B 3/0091; A61B 3/085; A61B 3/111; A61B 2034/107; A61B 2034/258; A61B 2090/3735; A61B 3/0008; A61B 3/1005; A61B 3/102; A61B 3/117; A61B 34/25; A61B 5/0036; A61B 5/7425; A61B 5/748; A61F 2/16; A61F 2/1618; A61F 2240/002; A61F 2250/006; A61F 9/00736; A61F 9/00754; A61F 9/008; A61F 9/009

See application file for complete search history.

(56) References Cited

U.S. PATENT DOCUMENTS

| | | |
|---|---|---|
| 9,782,064 B1 | 10/2017 | Linder |
| 2009/0281552 A1 | 11/2009 | Hiramatsu et al. |
| 2017/0156583 A1 | 6/2017 | Seesselberg |
| 2017/0290502 A1 | 10/2017 | Linder |
| 2019/0209242 A1* | 7/2019 | Padrick .................. A61B 34/10 |

* cited by examiner

*Primary Examiner* — Brandi N Thomas

(57) ABSTRACT

Systems and methods are presented for providing a graphical user interface (GUI) for assisting eye-care professionals in intraocular lens implantation planning in a two-stage process. During the first stage, first biometric data of a patient's eye is obtained. A first set of lens products comprising a first lens product is determined based on the first biometric data. A first grid is provided via the GUI to present the first set of lens products. During the second stage, second biometric data of the eye is obtained after an existing lens of the patient's eye is removed. A second set of lens products comprising a second lens product is determined based on the second biometric data. A second grid is provided via the GUI to present the second set of lens products and a difference between the first and second lens products.

13 Claims, 7 Drawing Sheets

Patient Name: John Doe ~302

IOL Calculation: Formula: Barrett   Target SEQ: 0.0   SIA: 0.3

Surgical Plan:
Pri Incision:
2.4mm @ 90 degrees

Sec Incision:
0.8mm @ 140 degrees 30 degrees @ 60
30 degrees @ 240

Depth 80%
Diameter 8.5mm
Nomogram: Verion

| | Power: 23.5D<br>APH REF: 2.00 | Power: 24.0D<br>APH REF: 2.00 | Power: 24.5D<br>APH REF: 2.00 |
|---|---|---|---|
| AST: T5 | | −1.03 | |
| AST: T4 | −0.74 | −0.74 | −0.74 |
| AST: T3 | 0.23 | −0.13 | 0.23 |
| AST: T2 | 0.68 | 0.68 | 0.68 |
| AST: T1 | | 1.43 | |

Figure 3

SYSTEMS AND METHODS FOR PROVIDING A GRAPHICAL USER INTERFACE FOR INTRAOCULAR LENS IMPLANTATION PLANNING

BACKGROUND

Field of the Disclosure

The present disclosure relates to a graphical user interface for assisting eye-care professionals in intraocular lens implantation planning according to various embodiments of the disclosure.

Description of Related Art

Intraocular lenses have been developed to replace natural lenses for patients who have eye conditions such as cataracts. For patients who have such eye conditions, a surgery may be performed by which the natural lens of the patient's eye is removed, and an artificial lens (e.g., an intraocular lens) is inserted into the eye to replace the natural lens. Given that different patients may have different eye geometries (e.g., require different lens prescriptions), lenses with different powers may be selected and used for the different patients to attain a target resulting vision (e.g., a target refraction value).

However, selecting the proper intraocular lens for a patient may not be an easy task. For example, since intraocular lenses are manufactured having discrete powers (e.g., 24.0 D, 24.5 D, etc.), eye-care professionals (ECPs) often times have to make compromises and select a lens that may produce similar, but not the exact target resulting vision for the patient. Furthermore, factors such as different lifestyle choices of the patients, eye surgery history of the patients, non-dominant eye preferences, and others may also influence the ECPs' decisions in choosing the lens. Therefore, there is a need in the art for providing a user interface for assisting ECPs in selecting intraocular lenses for patients.

SUMMARY

According to some embodiments, a method includes obtaining, by one or more hardware processors, first biometric data associated with an eye of a patient; determining, by the one or more hardware processors from a plurality of lens configurations, a first set of lens configurations based on the first biometric data and a target refraction value, wherein each lens configuration in the plurality of lens configurations corresponds to a particular spherical power and a particular toricity power, and wherein the first set of lens configurations comprises a first lens configuration having an associated resulting refraction value for the eye closest to the target refraction value based on the first biometric data; obtaining, by the one or more hardware processors, second biometric data associated with the eye of the patient after a natural lens of the eye has been removed; determining, by the one or more hardware processors from the plurality of lens configurations, a second set of lens configurations based on the second biometric data and the target refraction value, wherein the second set of lens configurations comprises a second lens configuration having an associated resulting refraction value for the eye closest to the target refraction value based on the second biometric data; presenting, by the one or more hardware processors on a graphical user interface (GUI) of a device, a grid representing the second set of lens configurations; and indicating, by the one or more hardware processors on the grid, a difference between the first lens configuration and the second lens configuration.

According to some embodiments, a system includes a non-transitory memory and one or more hardware processors configured to read instructions from the non-transitory memory to cause the system to perform operations comprising: obtaining first biometric data associated with an eye of a patient; determining, from a plurality of lens products, a first set of lens products based on the first biometric data, wherein each lens product in the plurality of lens products corresponds to a particular spherical power and a particular toricity power, and wherein the first set of lens products comprises a first lens product having an associated resulting refraction value for the eye closest to a target refraction value based on the first biometric data; obtaining second biometric data associated with the eye of the patient after an existing lens of the eye has been removed; determining, from the plurality of lens products, a second set of lens products based on the second biometric data, wherein the second set of lens products comprises a second lens product having an associated resulting refraction value for the eye closest to the target refraction value based on the second biometric data; and presenting, on a graphical user interface (GUI) of a device, a grid representing at least the first lens product and the second lens product.

According to some embodiments, a non-transitory machine-readable having stored thereon machine-readable instructions executable to cause a machine to perform operations including: obtaining first biometric data associated with an eye of a patient; determining, from a plurality of lens products, a first lens product having an associated resulting refraction value for the eye closest to a target refraction value based on the first biometric data; obtaining second biometric data associated with the eye of the patient after an existing lens of the eye has been removed; determining, from the plurality of lens products, a second lens product having an associated resulting refraction value for the eye closest to the target refraction value based on the second biometric data; and presenting, on a graphical user interface (GUI) of a device, a grid representing at least the first lens product and the second lens product.

BRIEF DESCRIPTION OF THE DRAWINGS

For a more complete understanding of the present technology, its features, and its advantages, reference is made to the following description, taken in conjunction with the accompanying drawings.

FIG. 3 illustrates a exemplary grid for presenting a set of lens products according to some embodiments.

Figure 1:
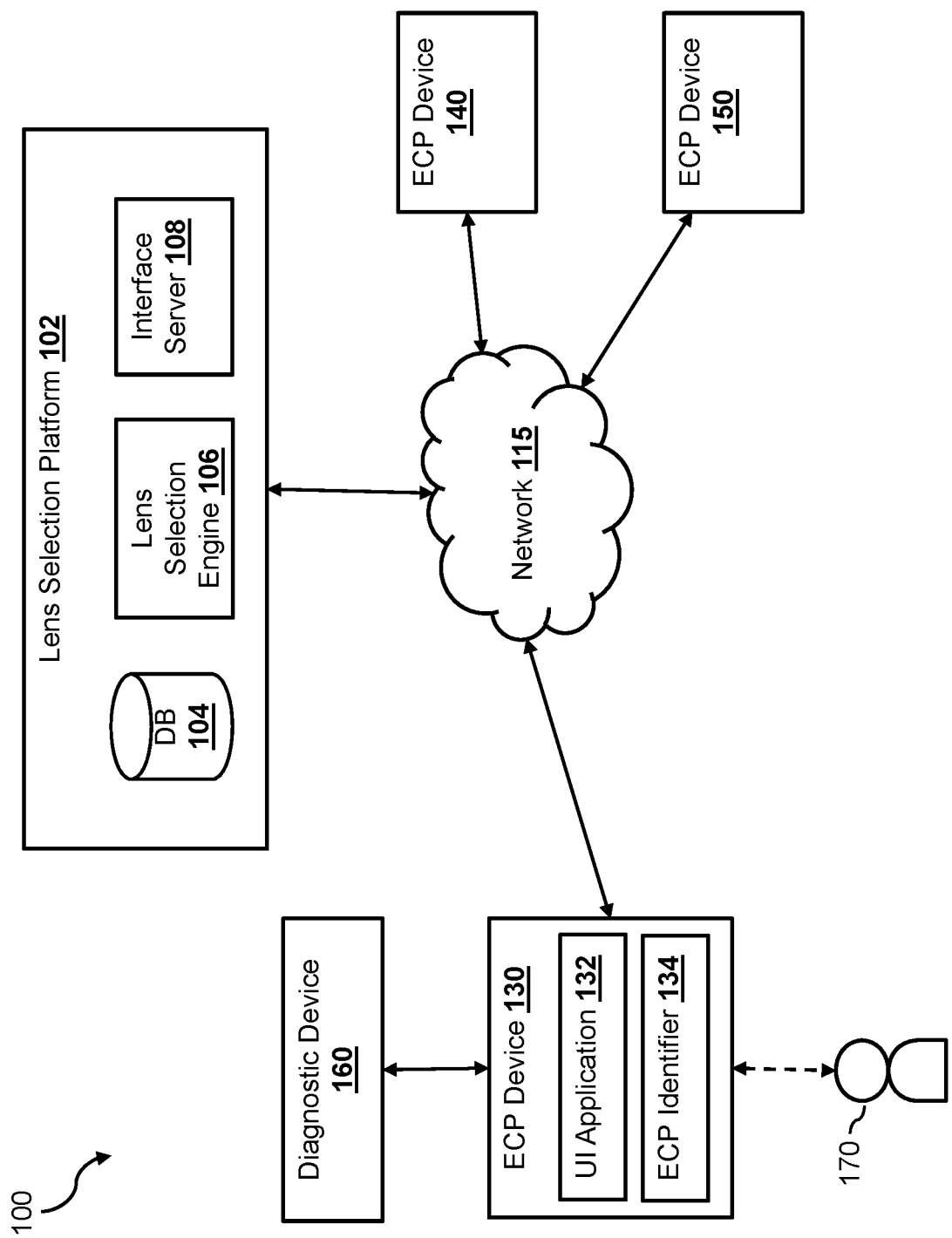
FIG. 1 is a diagram of a system for lens selection according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

The technology described below involves systems and methods to provide a graphical user interface (GUI) for assisting eye-care professionals (ECPs) (e.g., ophthalmologists) in intraocular lens implantation planning in a two-stage process. In some embodiments, a lens selection system may be provided to assist an ECP for selecting intraocular lenses for a patient. The lens selection system may present a GUI, on a device associated with ECP. During the first stage of the two-stage process, through the GUI presented on the device, the lens selection system may obtain first biometric data associated with an eye of the patient. For example, the ECP may use a diagnostic device to measure eye geometries of the eye such as an axial length, a corneal power, an anterior chamber depth, a lens thickness, a white-to-white corneal diameter, and possibly other measurements prior to performing a surgery on the eye. The ECP may then provide such eye geometries to the lens selection system via the GUI. In some embodiments, the diagnostic device may automatically provide the measured eye geometries to the GUI (e.g., automatically fill-in the data fields on the GUI). In some embodiments, the ECP may also provide a desirable post-surgery outcome, such as a target vision (e.g., a target refraction value), for the patient's eye to the lens selection system via the GUI.

Based on the first biometric data and the target refraction value, the lens selection system may select, from multiple lens products, a first lens product for the patient using one or more lens selection algorithms, which will be described in more detail below. In some embodiments, each lens product may have a distinct lens configuration, which specifies one or more corresponding powers (e.g., a corresponding spherical power and a corresponding toricity power, etc.) of the lens product. The lens selection system may select the first lens product by determining that the first lens product, among the multiple lens product available to the ECP, produces an estimated resulting vision (e.g., an estimated resulting refraction value) for the patient's eye that is closest to the target vision (e.g., the target refraction value) based on the first biometric data. As discussed above, lens products may be manufactured in discrete powers, and not every lens power is available to the ECP. For example, a family of lens products may include lenses having spherical powers separated by steps of 0.5 spherical powers (e.g., 24.0 D, 24.5 D, 25.0 D, etc.). Thus, a lens product having a spherical power in between the steps (e.g., 24.3 D) may not be available to the ECP.

In some embodiments, the lens selection system may use one or more algorithm (e.g., a Barrett Universal formula, a Haigis formula, a Hoffer Q formula, a Holladay formula, an SRK formula, etc.) to predict a lens power needed for the patient's eye to achieve the target vision based on the first biometric data of the patient. For example, the lens selection system may use the first biometric data, which includes the axial length, the corneal power, the anterior chamber depth, the lens thickness, the white-to-white corneal diameter of the patient's eye measured by the ECP as inputs for the Barrett Universal formula, and may determine, based on the Barrett Universal formula, a desired power (e.g., a desired spherical power, a desired toricity power, etc.) for the patient's eye. However, since the lens products available to the ECP may not include a lens product that has the exact desired power, the lens selection system may select a lens product, from the lens products available to the ECP, having a lens configuration closest to the desired power as the first lens product. For example, when the calculated desired power for the patient's eye include a spherical power of 24.1 D and a toricity power of T3, the lens selection system may select a lens product with a lens configuration that specifies a spherical power of 24.0 D and a toricity power of T3 as the first product for the patient's eye.

In addition to the first lens product, the lens selection system may also determine a first group of lens products based on the first lens product for the patient. The lens selection system may determine the first group of lens products under two different approaches. Under a first approach, the lens selection system may determine, from the different lens products available to the ECP, the first group of lens products that have lens configurations closest to the first lens configuration of the first lens product (or closest to the desired power). For example, when the first lens product has a first lens configuration that specifies a spherical power of 24.0 D and a toricity power of T3, the lens selection system may select lens products having spherical powers and/or toricity powers most similar (e.g., closest) to the first lens configuration of the first product as part of the first group of lens products. Using the example discussed above, for the first lens product having the first lens configuration that specifies a spherical power of 24.0 D and a toricity power of T3, the lens selection system may select lens products having lens configurations that specify the same toricity power of T3 (as the first lens configuration), but varying the spherical power (e.g., 23.5 D, 24.5 D, etc.) as part of the first group of lens products. Similarly, the lens selection system may select lens products having lens configurations that specify the same spherical power of 24.0 D (as the first lens configuration), but varying the toricity power (e.g., T2, T4, etc.) as part of the first group of lens products. In addition, the lens selection system may select lens products having lens configurations that specify similar (but not the same) spherical powers (e.g., 23.5 D, 24.5 D) and similar (but not the same) toricity powers (e.g., T2, T4, etc.).

Under a second approach, the lens selection system may determine, from the different lens products available to the ECP, the first group of lens products that would produce estimated resulting vision (e.g., estimated resulting refraction values) closest to the target vision (e.g., the target refraction value) based on the formula. The two approaches usually would produce the same group of lens products based on the first lens product, but not always. Therefore, it is beneficial for the lens selection system to be able to choose (or enable the ECP to choose) one of the two approaches in selecting the first group of lens products. The lens selection system may select any number of lens products (e.g., 4, 8, 10, etc.) for the first group of lens products using either approach.

In some embodiments, the lens selection system may present, via the GUI, the first lens product and the first group of lens products selected for the patient's eye. In some embodiments, the lens selection system may present the first lens product and the first group of lens products in a grid (e.g., a first grid) having two dimensions, where a first dimension corresponds to the spherical power and a second dimension corresponds to the toricity power. The lens selection system may present the first lens product (e.g., the lens product that would produce an estimated resulting vision closest to the target vision or the lens product having a lens configuration that specifies a spherical power and a toricity power closest to the desired power based on the first biometric data) at the center of the first grid. The lens selection system may then present the lens products in the first group of lens products around the first lens product. For example, the lens selection system may present lens products in the first group of lens products having the same toricity power (varying spherical power) along the first dimension of the first grid (e.g., to the left and right of the first lens product), and may present lens products in the first group of lens products having the same spherical power (varying toricity power) along the second dimension of the first grid (e.g., on the top and bottom of the first lens product). The lens selection system may then present the remaining lens products within the first group (e.g., lens products that vary both spherical and toricity powers from the first lens product) on the first grid along the first dimension with other lens products having the same toricity power and along the second dimension with other lens products having the same spherical power. As such, lens products having lens configurations more similar to the first lens product are presented closer to the first lens product on the first grid, and lens products having lens configurations less similar to (e.g., more different from) the first lens product are presented farther away from the first lens product on the first grid. In other words, the distance between a lens product and the first lens product on the first grid indicates how similar the lens configurations are between the lens product and the first lens product.

The grid presentation of the lens products based on the two dimensions (e.g., the spherical power dimension and the toricity power dimension) enhances the way that the lens products selected for the patient are presented to the ECP. As discussed above, the ECP may not always select the lens product that produces an estimated resulting vision closest to the target vision for the patient's eye. For example, the ECP may select a different lens product (other than the first lens product) for the patient's eye due to factors such as lifestyle choices of the patient, eye surgery history of the patient, non-dominant eye preference of the patient. Furthermore, the calculation of the desired power at this first stage of the two-stage process may not be accurate, as the measurements of the eye geometries that make up the first biometric data are estimated measurements and may not be accurate. As such, the lens product that the ECP may choose for implanting into the patient's eye during the surgery may be different. The grid presentation enables the ECP to select multiple lens products (e.g., lens products that are similar to the first lens products) for preparation of the surgery such that the lens product that is eventually selected by the ECP for implanting into the patient's eye is ready during surgery.

In some embodiments, the lens selection system may obtain second biometric data of the patient's eye during the second stage of the two-stage process. During the second stage of the two-stage process, the ECP has removed an existing lens (e.g., a natural lens) from the patient's eye, for example, during an eye surgery. The patient's eye, after removal of existing lens, will be referred to as "aphakic." After removing the existing lens from the patient's eye, the ECP may measure the eye geometry again to obtain second biometric data. Since the second biometric data is obtained after the lens is removed, the measurements are generally more accurate than the first biometric data, which was obtained prior to the removal of the lens. In some embodiments, the second biometric data may include a refraction value (e.g., obtained by refracting the aphakic patient, a wavefront measurement, etc.). Thus, the lens selection system may obtain, via the GUI, the second biometric data from the ECP.

Based on the second biometric data and the target refraction value, the lens selection system may select, from multiple lens products, a second lens product for the patient. The second lens product may have a second lens configuration that specifies a spherical power and a toricity power. In some embodiments, the lens selection system may use one or more aphakic-based intraocular lens prediction formulas to predict a lens power needed for the patient's eye to achieve the target vision based on the second biometric data of the patient. For example, the lens selection system may use the second biometric data, which includes a refraction value of the patient's eye, measured by the ECP after the lens of the patient's eye has been removed, as inputs for the aphakic-based formula, and may determine, based on the aphakic-based formula, a desired power (e.g., a desired spherical power, a desired toricity power, etc.) for the patient's eye. However, since the lens products available to the ECP may not include a lens product that has the exact desired power, the lens selection system may select a lens product, from the lens products available to the ECP, having a lens configuration closest to the desired power as the second lens product. For example, when the calculated desired power for the patient's eye include a spherical power of 24.4 D and a toricity power of T2, the lens selection system may select a lens product with a lens configuration that specifies a spherical power of 24.5 D and a toricity power of T2 as the second product for the patient's eye.

The second lens product may have the second lens configuration similar to the first lens configuration of the first lens product, and as such, the second lens product may be included in the first group of lens products. In some embodiments, the lens selection system may identify the second lens product in the first grid, and may modify the first grid by highlighting the second lens product in the first grid. For example, the lens selection system may insert a marker in the area where the second lens product is presented. If the second lens product is presented in a box within the first grid, the lens selection system may increase a thickness of the edges of the box. In some embodiments, the lens selection system may change a background color/pattern of the presentation of the second lens product. The lens selection system may then present the modified first grid via the GUI for the ECP. The highlighting of the second lens product in the modified first grid provides an indication of a distance between the first lens product and the second lens product in the modified first grid, thereby indicating a deviation between the first lens product and the second lens product.

In some embodiments, in addition to determining the second lens product, the lens selection system may also determine a second group of lens products based on the second lens product (and the second biometric data) for the patient. Similar to selecting the first group of lens products, the lens selection system may determine the second group of lens products under the two different approaches. Under the first approach, the lens selection system may determine, from the different lens products available to the ECP, the second group of lens products that have lens configurations closest to the second lens configuration of the second lens product (or closest to the desired power). For example, when the second lens product has a second lens configuration that specifies a spherical power of 24.5 D and a toricity power of T2, the lens selection system may select lens products having spherical powers and/or toricity powers most similar (e.g., closest) to the second lens configuration of the second product as part of the second group of lens products. Using the example discussed above, for the second lens product having the second lens configuration that specifies a spherical power of 24.5 D and a toricity power of T2, the lens selection system may select lens products having lens configurations that specify the same toricity power of T2 (as the second lens configuration), but varying the spherical power (e.g., 24.0 D, 25.0 D, etc.) as part of the second group of lens products. Similarly, the lens selection system may select lens products having lens configurations that specify the same spherical power of 24.0 D (as the second lens configuration), but varying the toricity power (e.g., T2, T4, etc.) as part of the first group of lens products. In addition, the lens selection system may select lens products having lens configurations that specify similar (but not the same) spherical powers (e.g., 24.0 D, 25.0 D) and similar (but not the same) toricity powers (e.g., T2, T4, etc.).

Under the second approach, the lens selection system may determine, from the different lens products available to the ECP, the second group of lens products that would produce estimated resulting vision (e.g., estimated resulting refraction values) for the patient's eye closest to the target vision (e.g., the target refraction value) based on the aphakic-based formula. Similar to determining the first group of lens products, the lens selection system of some embodiments may select any number of lens products (e.g., 4, 8, 10, etc.) for the second group of lens products using either approach. The number of lens products selected for the second group may be the same or different from the number of lens products selected for the first group.

In some embodiments, in addition to or instead of presenting the modified first grid, the lens selection system may generate a second grid for presenting the second lens product and the second group of lens products selected for the patient's eye. Similar to the first grid, the second grid also has two dimensions where a first dimension corresponds to the spherical power and a second dimension corresponds to the toricity power. The lens selection system may present the second lens product (e.g., the lens product that would produce an estimated resulting vision closest to the target vision or the lens product having a lens configuration that specifies a spherical power and a toricity power closest to the desired power based on the second biometric data) at the center of the second grid. The lens selection system may then present the lens products in the second group of lens products around the second lens product. For example, the lens selection system may present lens products in the second group of lens products having the same toricity power (varying spherical power) along the first dimension of the first grid (e.g., to the left or right of the second lens product), and may present lens products in the second group of lens products having the same spherical power (varying toricity power) along the second dimension of the second grid (e.g., on top or bottom of the second lens product). The lens selection system may then present the remaining lens products within the second group (e.g., lens products that vary both spherical and toricity powers from the second lens product) on the second grid along the first dimension with other lens products having the same toricity power and along the second dimension with other lens products having the same spherical power. As such, lens products having lens configurations more similar to the second lens product are presented closer to the second lens product on the second grid, and lens products having lens configurations less similar to (e.g., more different from) the second lens product are presented farther away from the second lens product on the second grid. In other words, the distance between a lens product and the second lens product on the second grid indicates how similar the lens configurations are between the lens product and the second lens product. The lens selection system may then present, via the GUI, the second grid to the ECP.

As discussed above, the first lens product may have the first lens configuration similar to the second lens configuration of the second lens product, and as such, the first lens product may be included in the second group of lens products. In some embodiments, the lens selection system may identify the first lens product in the second grid, and may modify the second grid by highlighting the first lens product in the second grid. For example, the lens selection system may insert a marker in the area where the first lens product is presented on the second grid. If the first lens product is presented in a box within the second grid, the lens selection system may increase a thickness of the edges of the box. In some embodiments, the lens selection system may change a background color/pattern of the presentation of the first lens product. The lens selection system may then present the modified second gird via the GUI for the ECP. Similar to the modified first grid, the highlighting of the first lens product in the modified second grid provides an indication of a distance between the first lens product and the second lens product in the modified second grid, thereby indicating a deviation between the first lens product and the second lens product.

The indication of the differences between the first lens product and the second lens product (e.g., via the modified first grid, the modified second grid, etc.) may enable the ECP to perform necessary corrective actions before selecting a lens product and implanting the lens product into the patient's eyes. For example, if the differences are larger than a predetermined threshold, the ECP may perform the measurement of the eye parameters again. Thus, when it is determined that the differences between the first lens product and the second lens product is larger than the predetermined threshold, the lens selection system may also perform an action to provide a warning to the ECP, for example, by providing an alert on the GUI indicating the large differences between the first lens product and the second lens product.

FIG. 1 illustrates a system 100 within which the lens selection system as discussed herein may be implemented according to some embodiments. System 100 includes a lens selection platform 102 coupled with one or more ECP devices, such as ECP devices 130, 140, and 150 via a network 115. Each of the ECP devices may also be communicatively coupled to a diagnostic device. For example, the ECP device 130 is communicatively coupled to a diagnostic device 160 (e.g., via an internal network, a wired or wireless connection, etc.). In some examples, network 115 may include one or more switching devices, routers, local area networks (e.g., an Ethernet), wide area networks (e.g., the Internet), and/or the like. While it is shown in this figure that the lens selection platform 102 is remote from the ECP devices, in some embodiments, a portion of or all of the lens selection platform may also be implemented within each of the ECP devices 130-150 and/or the diagnostic device 160 so that the functionality of the lens selection system can be executed locally at the ECP office.

Each of the ECP devices (e.g., the ECP devices 130, 140, and 150) may include a user interface (UI) application and an ECP identifier. For example, the ECP device 130 includes a UI application 132 and an ECP identifier 134. The UI application 132 may be used by a corresponding ECP (e.g., the ECP 170) to interact with the lens selection platform 102. For example, the UI application 132 may be a web browser or a client application (e.g., a mobile application). The ECP 170, via the UI application 132 may access a graphical user interface (GUI), such as a webpage generated and/or hosted by the lens selection platform 102. The ECP identifier 134 is an identifier that uniquely identifies the ECP 170 among multiple ECP serviced by the lens selection platform 102.

The lens selection platform 102 includes a database 104, a lens selection engine 106, and an interface server 108. The database 104 may store information associated with lens products (e.g., different families of lens products including the lens configurations that are available with each family of lens products, etc.). For example, based on an ECP identifier (e.g., the ECP identifier 134), the lens selection platform 102 may determine which family (families) of lens products is/are available to the ECP by querying the database 104. The interface server 108, in some embodiments, is configured to provide a user interface (e.g., a graphical user interface (GUI), etc.) on the ECP devise 130, 140, and 150, via which the ECPs such as the ECP 170 may interact with the lens selection platform 102. For example, the interface server 108 of some embodiments may include a web server that hosts a website associated with the lens selection platform 102. The interface server 108 may generate and/or store one or more interactive webpages that may present on the ECP devices via the UI application (e.g., the UI application 132). In another example, the interface server 108 may include an application server that interacts with a client application (e.g., the UI application 132) via a protocol (e.g., REST protocol, etc.).

In some embodiments, an ECP (e.g., the ECP 170) may obtain biometric data of an eye of a patient (e.g., before and/or after removal of an existing lens in the patient's eye). For example, the ECP 170 may use the diagnostic device 160 to measure eye geometries of the patient's eye. Upon obtaining the biometric data, the ECP 170 may provide, via the UI application (e.g., the UI application 132) and the user interface provided by the interface server 108, biometric data of an eye of a patient (e.g., before and/or after removal of an existing lens in the patient's eye). In some embodiments, the ECP device 130 may establish a connection with the diagnostic device 160 and automatically obtain the biometric data from the diagnostic device 160, and may also automatically use the obtained biometric data to fill-in the data fields on the user interface such that the ECP 170 may not need to manually provide the biometric data to the user interface. Based on the biometric data received from an ECP device, the lens selection engine 106 may generate a presentation of one or more lens products that are available to the ECP, and selected for the patient's eye based on the biometric data. In some embodiments, the interface server may present the one or more lens products in a grid. The grid may indicate an optimal lens product (e.g., a first lens product) for the patient's eye selected based on first biometric data obtained by the ECP prior to the removal of an existing lens in the patient's eye, an optimal lens product (e.g., a second lens product) for the patient's eye selected based on second biometric data obtained by the ECP after the removal of the existing lens in the patient's eye, and a deviation (e.g., a different in powers) between the first lens product and the second lens product.

Figure 2:
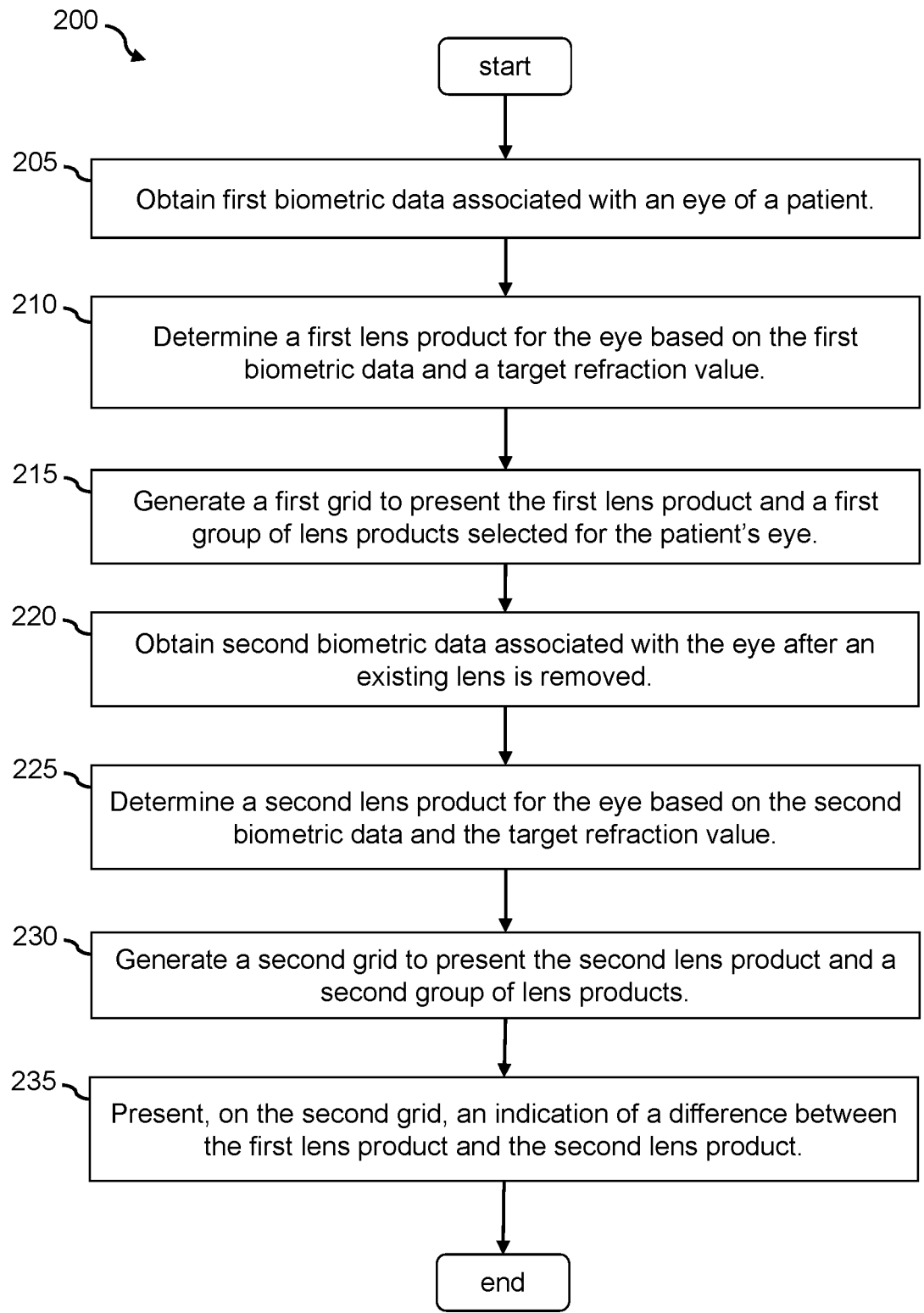
FIG. 2 illustrates a process of providing a graphical user interface for presenting lens products for a patient according to some embodiments.

FIG. 2 illustrates a process 200 for providing a user interface to an ECP for selecting a lens product for a patient's eye using a two-stage process according to one embodiment of the disclosure. In some embodiments, the process 200 may be performed by the lens selection platform 102, the ECP devices 130-150, and/or the diagnostic device 160. The process 200 begins by obtaining (at step 205) first biometric data associated with an eye of a patient. For example, during the first stage of the two-stage process, an ECP (e.g., the ECP 170) may measure eye geometries of an eye of a patient prior to performing a surgery on the eye. In some embodiments, the ECP 170 may use the diagnostic device 160 to measure the eye geometrics of the eye of the patient. The eye geometries may include an axial length, a corneal power, an anterior chamber depth, a lens thickness, a white-to-white corneal diameter, and possibly other measurements. The ECP 170 may then provide such eye geometries to the lens selection system. As discussed above, in some embodiments, the interface server 108 of the lens selection platform 102 may provide a GUI on the ECP device 130 of the ECP 170. For example, the ECP may use the UI application 132 to access the GUI (e.g., a webpage) associated with the lens selection platform 102. The GUI may include a mechanism (e.g., input fields) configured to receive the eye geometries (e.g., the first biometric data) from the ECP 170. The ECP 170 may manually enter the first biometric data to on the GUI before submitting the first biometric data to the lens selection platform 102. However, in the cases where the diagnostic device 160 is connected to the ECP device 130, the diagnostic device may automatically transmit the first biometric data to the ECP device and automatically use the first biometric data to fill-in the data fields on the GUI. In some embodiments, the ECP 170 may also provide a desirable post-surgery outcome, such as a target vision (e.g., a target refraction value), for the patient's eye to the lens selection platform 102 via the GUI. In some embodiments, the GUI may be configured to transmit the first biometric data provided by the ECP 170, the target refraction value, and the ECP identifier 134 to the lens selection platform 102 (e.g., in response to the ECP selecting a "submit" button on the GUI).

The process 200 then determines (at step 210) a first lens product for the eye based on the first biometric data and a target refraction value. Upon obtaining the first biometric data and the ECP identifier 134 from the ECP device 130, the lens selection engine 106 may first query the database 104 based on the ECP identifier 134 to retrieve a set of lens products (e.g., one or more family of lens products) that are available to the ECP 170. In some embodiments, each lens product may have a distinct lens configuration, which specifies one or more corresponding powers (e.g., a corresponding spherical power and a corresponding toricity power, etc.) of the lens product. The lens selection system may select the first lens product by determining that the first lens product, among the multiple lens product available to the ECP 170, produces an estimated resulting vision (e.g., an estimated resulting refraction value) for the patient's eye that is closest to the target vision (e.g., the target refraction value). As discussed above, lens products may be manufactured in discrete powers, and not every lens power is available to the ECP 170. For example, a family of lens products that are available to the ECP 170 may include lenses having spherical powers separated by steps of 0.5 spherical powers (e.g., 24.0 D, 24.5 D, 25.0 D, etc.). Thus, a lens product having a spherical power in between the steps (e.g., 24.3 D) may not be available to the ECP 170.

In some embodiments, the lens selection engine 106 may use one or more algorithm (e.g., a Barrett Universal formula, a Haigis formula, a Hoffer Q formula, a Holladay formula, an SRK formula, etc.) to predict a lens power needed for the patient's eye to achieve the target vision based on the first biometric data of the patient. For example, the lens selection engine 106 may use the first biometric data, which includes the axial length, the corneal power, the anterior chamber depth, the lens thickness, the white-to-white corneal diameter of the patient's eye measured by the ECP 170 as inputs for the Barrett Universal formula, and may determine, based on the Barrett Universal formula, a desired power (e.g., a desired spherical power, a desired toricity power, etc.) for the patient's eye. However, since the lens products available to the ECP 170 may not include a lens product that has the exact desired power, the lens selection engine 106 may select a lens product, from the lens products available to the ECP 170, having a lens configuration closest to the desired power as the first lens product. For example, when the calculated desired power for the patient's eye include a spherical power of 24.1 D and a toricity power of T3, the lens selection engine 106 may select a lens product with a lens configuration that specifies a spherical power of 24.0 D and a toricity power of T3 as the first product for the patient's eye.

The process 200 then generates (at step 215) a first grid to present the first lens product and a first group of lens products selected for the patient's eye. In some embodiments, in addition to the first lens product, the lens selection engine 106 may also determine a first group of lens products based on the first lens product for the patient. The lens selection engine 106 may determine the first group of lens products under two different approaches. Under a first approach, the lens selection engine 106 may determine, from the different lens products available to the ECP, the first group of lens products that have lens configurations closest to the first lens configuration of the first lens product (or closest to the desired power). For example, when the first lens product has a first lens configuration that specifies a spherical power of 24.0 D and a toricity power of T3, the lens selection engine 106 may select lens products having spherical powers and/or toricity powers most similar (e.g., closest) to the first lens configuration of the first product as part of the first group of lens products. Using the example discussed above, for the first lens product having the first lens configuration that specifies a spherical power of 24.0 D and a toricity power of T3, the lens selection engine 106 may select lens products having lens configurations that specify the same toricity power of T3 (as the first lens configuration), but varying the spherical power (e.g., 23.5 D, 24.5 D, etc.) as part of the first group of lens products. Similarly, the lens selection engine 106 may select lens products having lens configurations that specify the same spherical power of 24.0 D (as the first lens configuration), but varying the toricity power (e.g., T2, T4, etc.) as part of the first group of lens products. In addition, the lens selection engine 106 may select lens products having lens configurations that specify similar (but not the same) spherical powers (e.g., 23.5 D, 24.5 D) and similar (but not the same) toricity powers (e.g., T2, T4, etc.).

Under a second approach, the lens selection engine 106 may determine, from the different lens products available to the ECP 170, the first group of lens products that would produce estimated resulting vision (e.g., estimated resulting refraction values) closest to the target vision (e.g., the target refraction value) based on the formula. The two approaches usually would produce the same group of lens products based on the first lens product, but not always. Therefore, it is beneficial for the lens selection engine 106 to be able to choose (or enable the ECP 170 to choose via the GUI) one of the two approaches in selecting the first group of lens products. The lens selection system may select any number of lens products (e.g., 4, 8, 10, etc.) for the first group of lens products using either approach.

In one example, the lens selection engine 106 may select ten lens products having the following lens configurations as the first group of lens products: (a) a spherical power of 24.0 D and a toricity power of T4, (b) a spherical power of 24.0 D and a toricity power of T5, (c) a spherical power of 24.0 D and a toricity power of T2, (d) a spherical power of 24.0 D and a toricity power of T1, (e) a spherical power of 23.5 D and a toricity power of T3, (f) a spherical power of 24.5 D and a toricity power of T3, (g) a spherical power of 23.5 D and a toricity power of T4, (h) a spherical power of 23.5 D and a toricity power of T2, (i) a spherical power of 24.5 D and a toricity power of T4, and (j) a spherical power of 24.5 D and a toricity power of T2.

In some embodiments, the lens selection engine 106 may use the interface server 108 to present, via the GUI, the first lens product and the first group of lens products selected for the patient's eye. In some embodiments, the interface server 108 may present the first lens product and the first group of lens products in a grid (e.g., a first grid). FIG. 3 illustrates an example GUI 300 provided by the interface server 108 to the ECP device 130. As shown in FIG. 3, the GUI 300 may indicate a patient's name 302 (e.g., John Doe), a formula used to select the lens products for the patient 304 (e.g., Barrett), and a target vision (e.g., a target refraction value) 306 (e.g., 0.0). In some embodiments, the lens selection platform 102 may enable, via the GUI 300, the ECP 170 to choose a different formula for calculating a desired power for the patient (e.g., a Haigis formula, a Hoffer Q formula, etc.).

The GUI 300 may also present information 308 associated with the planned surgery for the patient's eye, such as the primary incision information, the secondary incision information, etc. In some embodiments, the lens selection platform 102 may also provide, via the GUI 300, a presentation of the first lens product and the first group of lens products selected for the patient's eye based on the first biometric data obtained from the ECP 170 via the GUI 300. As shown, the interface server 108 provides a grid 310 on the GUI 300 for presenting the first lens product and the first group of lens products selected for the patient's eye. The grid 310 has two dimensions, where a first dimension (e.g., a horizontal dimension) corresponds to the spherical power and a second dimension (e.g., a vertical dimension) corresponds to the toricity power.

In some embodiments, the lens selection platform 102 may present the first lens product (e.g., the lens product that would produce an estimated resulting vision closest to the target vision or the lens product having a lens configuration that specifies a spherical power and a toricity power closest to the desired power based on the first biometric data) at the center of the grid 310. As shown, the first lens product having the first lens configuration (a spherical power of 24.0 D and a toricity power of T3) is presented in a box 312 at the center of the grid. In addition, the box 312 is highlighted (e.g., patterned background) to indicate to the ECP 170 that the lens product presented in the box 312 is the lens product having an estimated resulting vision closest to the target vision or the lens product having a lens configuration that specifies a spherical power and a toricity power closest to the desired power based on the first biometric data.

The lens selection platform 102 may also present the lens products in the first group of lens products around the first lens product in the grid 310. For example, the lens selection platform 102 may present lens products in the first group of lens products having the same toricity power (varying spherical power) along the first dimension of the first grid (e.g., on the left and right of the box 312 that presents the first lens product). In this example, the lens products in the first group of lens products having the same toricity power, such as a lens product having a spherical power of 23.5 D and a toricity power of T3 and a lens product having a spherical power of 24.5 D and a toricity power of T3 are presented to the left and to the right of the box 312, respectively. The lens selection platform 102 may present lens products in the first group of lens products having the same spherical power (varying toricity power) along the second dimension of the first grid (e.g., on the top and bottom of the box 312 that presents the first lens product). In this example, a lens product having a spherical power of 24.0 D and a toricity power of T4 and a lens product having a spherical power of 24.0 D and a toricity power of T5 are presented on top of the box 312, and a lens product having a spherical power of 24.0 D and a toricity power of T2 and a lens product having a spherical power of 24.0 D and a toricity power of T1 are presented on the bottom of the box 312.

The lens selection platform 102 may also present the remaining lens products within the first group (e.g., lens products that vary both spherical and toricity powers from the first lens product) on the grid 310 along the first dimension with other lens products having the same toricity power and along the second dimension with other lens products having the same spherical power. For example, a lens product having a spherical power of 23.5 D and a torcitiy power of T4 and a lens product having a spherical power of 24.5 D and a toricity power of T4 are presented on the same row (along the first dimension) of the grid 310 as the lens product having the spherical power of 24.0 D and the toricity power of T4. Similarly, a lens product having a spherical power of 23.5 D and a toricity power of T2 are presented on the same column as the lens product having the spherical power of 23.5 D and the toricity power of T3 on the grid 310.

As such, lens products within the first group having lens configurations more similar to the first lens product are presented closer to the first lens product (e.g., the box 312) on the grid 310, and lens products within the first group having lens configurations less similar to (e.g., more different from) the first lens product are presented farther away from the first lens product (e.g., the box 312) on the grid 310. In other words, the distance between a lens product and the first lens product on the grid 310 indicates how similar the lens configurations are between the lens product and the first lens product.

The grid presentation of the lens products based on the two dimensions (e.g., the spherical power dimension and the toricity power dimension) enhances the way that the lens products selected for the patient are presented to the ECP 170. As discussed above, the ECP 170 may not always select the lens product that produces an estimated resulting vision closest to the target vision for the patient's eye. For example, the ECP 170 may select a different lens product (other than the first lens product) for the patient's eye due to factors such as lifestyle choices of the patient, eye surgery history of the patient, non-dominant eye preference of the patient. Furthermore, the calculation of the desired power at this first stage of the two-stage process may not be accurate, as the measurements of the eye geometries that make up the first biometric data are estimated measurements and may not be accurate. As such, the lens product that the ECP 170 may ultimately choose for implanting into the patient's eye during the surgery may be different. The grid 310 enables the ECP 170 to select multiple lens products (e.g., lens products that are similar to the first lens products) for preparation of the surgery such that the lens product that is eventually selected by the ECP 170 for implanting into the patient's eye is ready during surgery.

Referring back to FIG. 2, after generating the first grid to present the first lens product and the first group of lens products, the process 200 obtains (at step 220) second biometric data associated with the eye after an existing lens is removed from the eye. In some embodiments, the lens selection platform 102 may obtain second biometric data of the patient's eye during the second stage of the two-stage process. During the second stage of the two-stage process, the ECP 170 may have removed an existing lens (e.g., a natural lens) from the patient's eye. After removing the lens from the patient's eye, the ECP 170 may measure the eye geometry again to obtain second biometric data. Since the second biometric data is obtained after the lens is removed, the measurements are theoretically more accurate than the first biometric data, which was obtained prior to the removal of the lens. In some embodiments, the second biometric data may include a refraction value (e.g., obtained by refracting the aphakic patient, a wavefront measurement, etc.). Thus, the lens selection engine 106 may obtain, via the GUI, the second biometric data from the ECP 170.

The process 200 then determines (at step 225) a second lens product for the eye based on the second biometric data and the target refraction value. For example, based on the second biometric data and the target refraction value, the lens selection engine 106 may select, from the multiple lens products available to the ECP 170, a second lens product for the patient's eye. The second lens product may have a second lens configuration that specifies a spherical power and a toricity power. In some embodiments, the lens selection engine 106 may use one or more aphakic-based intraocular lens prediction formulas to predict a lens power needed for the patient's eye to achieve the target vision based on the second biometric data of the patient. For example, the lens selection engine 106 may use the second biometric data, which includes a refraction value of the patient's eye, measured by the ECP 170 after the lens of the patient's eye has been removed, as inputs for the aphakic-based formula, and may determine, based on the aphakic-based formula, a desired power (e.g., a desired spherical power, a desired toricity power, etc.) for the patient's eye. However, since the lens products available to the ECP 170 may not include a lens product that has the exact desired power, the lens selection engine 106 may select a lens product, from the lens products available to the ECP, having a lens configuration closest to the desired power as the second lens product. For example, when the calculated desired power for the patient's eye include a spherical power of 24.4 D and a toricity power of T2, the lens selection system may select a lens product with a lens configuration that specifies a spherical power of 24.5 D and a toricity power of T2 as the second product for the patient's eye.

The second lens product may have the second lens configuration similar to the first lens configuration of the first lens product, and as such, the second lens product may be included in the first group of lens products. In some embodiments, the lens selection engine 106 may identify the second lens product in the grid 310, and may modify the grid 310 by highlighting the second lens product in the grid 310. For example, the interface server 108 may insert a marker in the area where the second lens product is presented. If the second lens product is presented in a box within the grid 310, the lens selection system may increase a thickness of the edges of the box. In some embodiments, the interface server 108 may change a background color/pattern of the presentation of the second lens product on the grid 310. The lens selection system may then present the modified grid via the GUI for the ECP 170.

Figure 4:
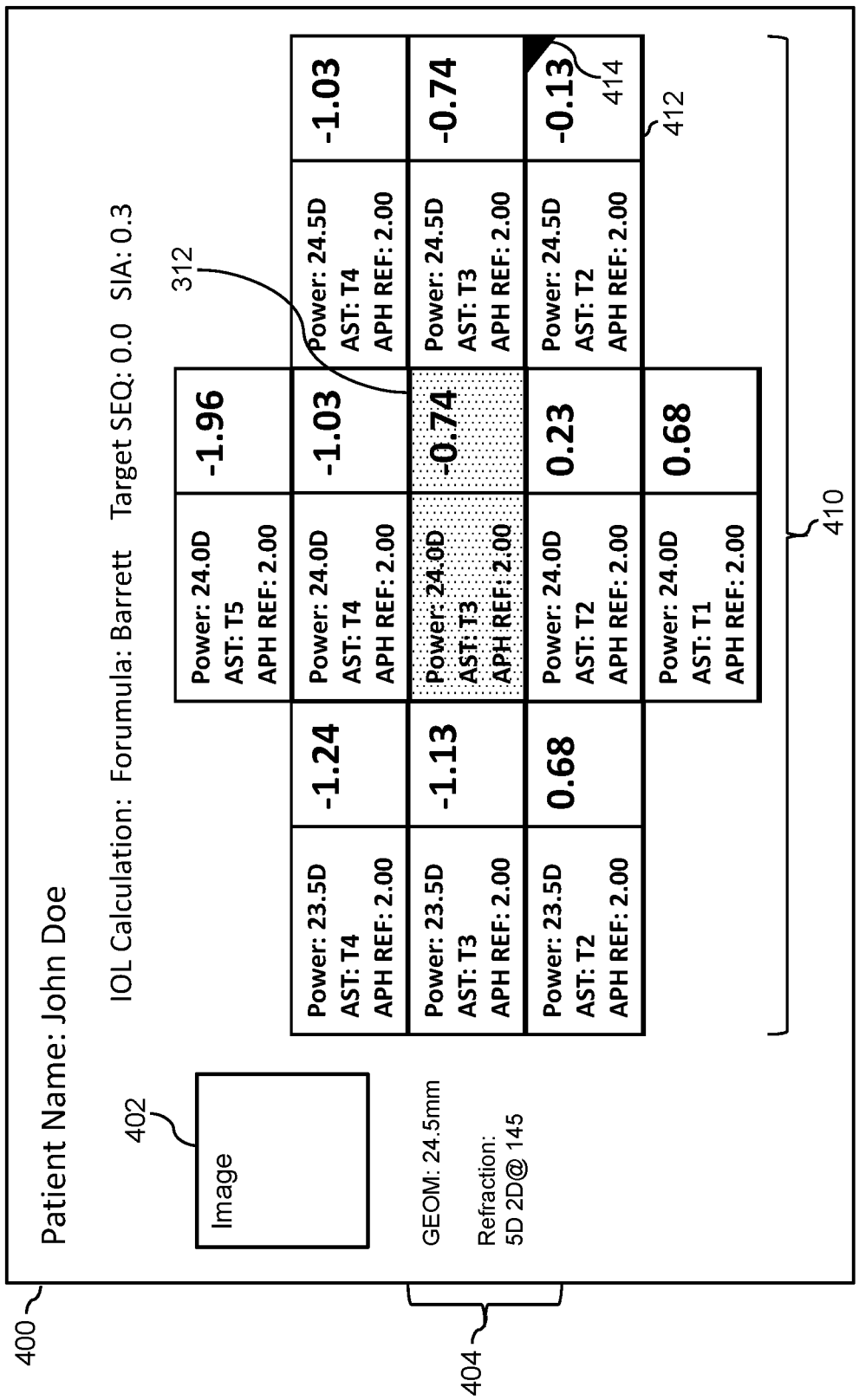
FIG. 4 illustrates a modified grid for presenting a set of lens products according to some embodiments.

FIG. 4 illustrates a GUI 400 that is presented to the ECP 170 during the surgery of the patient's eye. As shown, the GUI 400 includes the name of the patient, an image 402 of the patient's eye after the existing lens has been removed, and measurements (e.g., the second biometric data) 404 of the patient's eye that were obtained after the existing lens of the eye has been removed. The second biometric data may include a geometry measurement of the eye (e.g., 24.5 mm) and a refraction value of the eye. In addition, the GUI 400 includes a grid 410 that is based on modifying the grid 310 according to the techniques described herein.

As shown, the grid 410 is almost identical to the grid 310 that presents the first lens product and the first group of lens product, except that a box 412 that presents the second lens product is highlighted. In this example, the box 412 includes a marker 414 to indicate that the lens product presented in the box 414 is the second lens product. In some embodiments, the box 312 (that presents the first lens product) is highlighted differently from the box 412 to differentiate the first lens product and the second lens product. The highlighting of the second lens product in the modified first grid provides an indication of a distance between the first lens product and the second lens product in the modified first grid, thereby indicating a deviation (e.g., a difference) between the first lens product and the second lens product to the ECP 170.

In some embodiments, in addition to determining the second lens product, the lens selection system may also determine a second group of lens products based on the second lens product (and the second biometric data) for the patient and generate a second grid for presenting the second lens product and the second group of lens products. Thus, at step 230, the process 200 generates a second grid to present the second lens and a second group of lens products. Similar to selecting the first group of lens products, the lens selection engine 106 may determine the second group of lens products based on the second lens product (and the second biometric data) under the two different approaches as discussed herein. Under the first approach, the lens selection engine 106 may determine, from the different lens products available to the ECP 170, the second group of lens products that have configurations closest to the second lens configuration of the second lens product (or closest to the desired power). For example, when the second lens product has a second lens configuration that specifies a spherical power of 24.5 D and a toricity power of T2, the lens selection system may select lens products having spherical powers and/or toricity powers most similar (e.g., closest) to the second lens configuration of the second product as part of the second group of lens products. Using the example discussed above, for the second lens product having the second lens configuration that specifies a spherical power of 24.5 D and a toricity power of T2, the lens selection engine 106 may select lens products having lens configurations that specify the same toricity power of T2 (as the second lens configuration), but varying the spherical power (e.g., 24.0 D, 25.0 D, etc.) as part of the second group of lens products. Similarly, the lens selection engine 106 may select lens products having lens configurations that specify the same spherical power of 24.0 D (as the second lens configuration), but varying the toricity power (e.g., T2, T4, etc.) as part of the first group of lens products. In addition, the lens selection engine 106 may select lens products having lens configurations that specify similar (but not the same) spherical powers (e.g., 24.0 D, 25.0 D) and similar (but not the same) toricity powers (e.g., T2, T4, etc.).

Under the second approach, the lens selection engine 106 may determine, from the different lens products available to the ECP 170, the second group of lens products that would produce estimated resulting vision (e.g., estimated resulting refraction values) for the patient's eye closest to the target vision (e.g., the target refraction value) based on the aphakic-based formula. Similar to determining the first group of lens products, the lens selection engine 106 of some embodiments may select any number of lens products (e.g., 4, 8, 10, etc.) for the second group of lens products using either approach. The number of lens products selected for the second group may be the same or different from the number of lens products selected for the first group.

In one example, the lens selection engine 106 may select ten lens products having the following lens configurations as the second group of lens products: (a) a spherical power of 24.5 D and a toricity power of T3, (b) a spherical power of 24.5 D and a toricity power of T4, (c) a spherical power of 24.5 D and a toricity power of T1, (d) a spherical power of 24.5 D and a toricity power of T0, (e) a spherical power of 24.0 D and a toricity power of T2, (f) a spherical power of 25.0 D and a toricity power of T2, (g) a spherical power of 24.0 D and a toricity power of T3, (h) a spherical power of 24.0 D and a toricity power of T1, (i) a spherical power of 25.0 D and a toricity power of T3, and (j) a spherical power of 25.0 D and a toricity power of T1.

Figure 5:
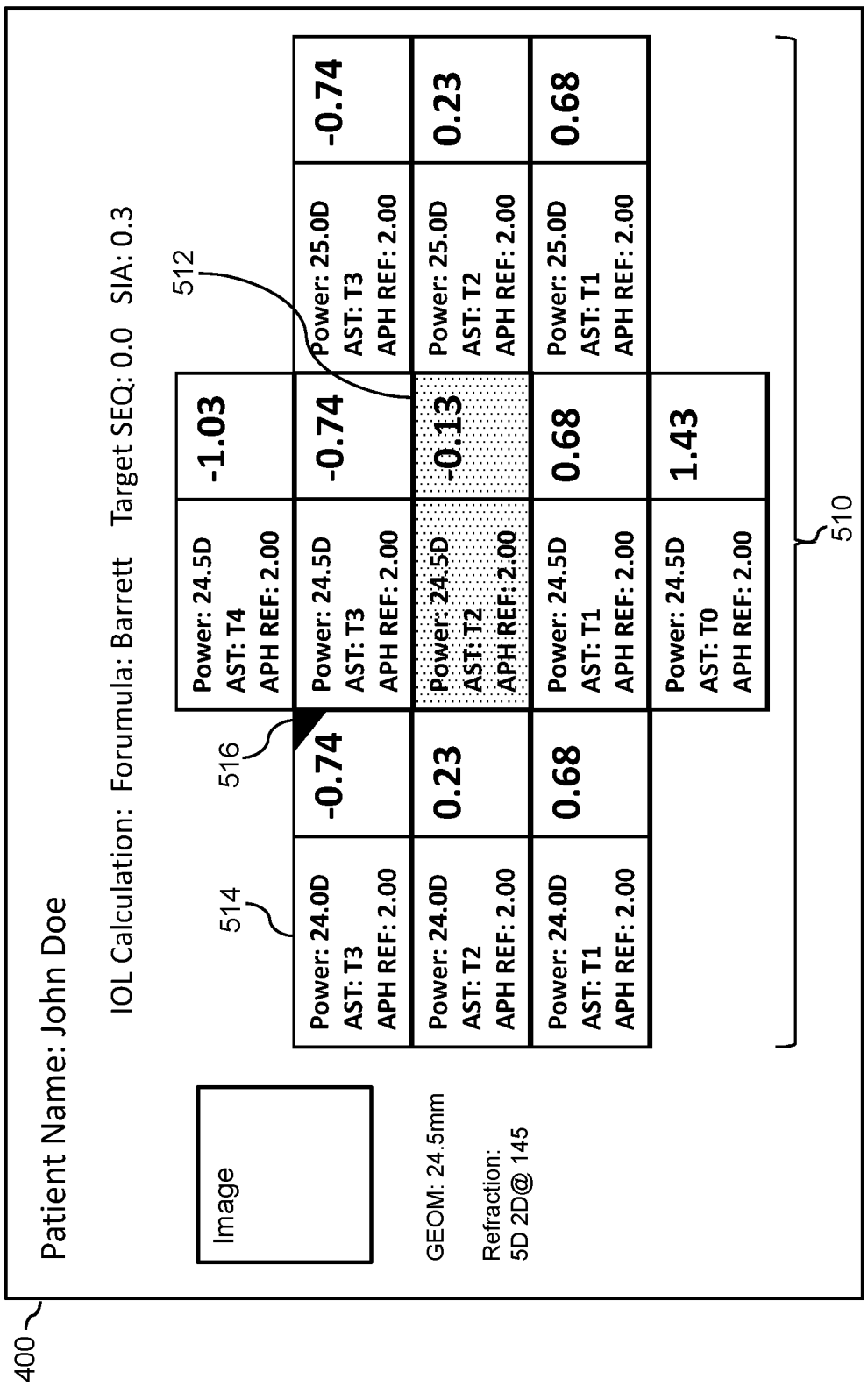
FIG. 5 illustrates another grid example for presenting a set of lens products according to some embodiments.

In some embodiments, in addition to or instead of modifying the first grid (e.g., the grid 310), the lens selection engine 106 may generate a second grid for presenting the second lens product and the second group of lens products selected for the patient's eye. FIG. 5 illustrates the GUI 400 displaying a grid 510 (e.g., the second grid) for presenting the second lens product and the second group of lens products. Similar to the first grid (e.g., the grid 310), the grid 510 also has two dimensions where a first dimension corresponds to the spherical power and a second dimension corresponds to the toricity power (the dimensions can correspond to the different powers, thus, in some embodiments, the second grid might have a first dimension that corresponds to the toricity power and a second dimension that corresponds to the spherical power). The lens selection engine 106 may present the second lens product (e.g., the lens product that would produce an estimated resulting vision closest to the target vision or the lens product having a lens configuration that specifies a spherical power and a toricity power closest to the desired power based on the second biometric data) at the center of the grid 510, for example, inside a box 512 at the center of the grid 510. The lens selection engine 106 may then present the lens products in the second group of lens products around the second lens product (e.g., the box 512) on the grid 510. For example, the lens selection engine 106 may present lens products in the second group of lens products having the same toricity power (varying spherical power) along the first dimension of the first grid (e.g., to the left of right of the second lens product). In this example, the lens products in the second group of lens products having the same toricity power as the second lens product, such as a lens product having a spherical power of 24.0 D and a toricity power of T2 and a lens product having a spherical power of 25.0 D and a toricity power of T2 are presented to the left and to the right of the box 512, respectively. The lens selection engine 106 may present lens products in the second group of lens products having the same spherical power (varying toricity power) along the second dimension of the second grid (e.g., on the top or bottom of the second lens product). In this example, a lens product having a spherical power of 24.5 D and a toricity power of T3 and a lens product having a spherical power of 24.5 D and a toricity power of T4 are presented on top of the box 512, and a lens product having a spherical power of 24.5 D and a toricity power of T1 and a lens product having a spherical power of 24.5 D and a toricity power of T0 are presented on the bottom of the box 512.

The lens selection engine 106 may then present the remaining lens products within the second group (e.g., lens products that vary both spherical and toricity powers from the second lens product) on the second grid along the first dimension with other lens products having the same toricity power and along the second dimension with other lens products having the same spherical power. For example, a lens product having a spherical power of 24.0 D and a torcitiy power of T3 and a lens product having a spherical power of 25.0 D and a toricity power of T3 are presented on the same row (along the first dimension) of the grid 510 as the lens product having the spherical power of 24.5 D and the toricity power of T3. Similarly, a lens product having a spherical power of 24.0 D and a toricity power of T1 are presented on the same column as the lens product having the spherical power of 24.0 D and the toricity power of T2 on the grid 510.

As such, lens products having lens configurations more similar to the second lens product are presented closer to the second lens product (e.g., the box 512) on the grid 510, and lens products having lens configurations less similar to (e.g., more different from) the second lens product are presented farther away from the second lens product (e.g., the box 512) on the grid 510. In other words, the distance between a lens product and the second lens product on the second grid indicates how similar the lens configurations are between the lens product and the second lens product.

The process 200 then presents (at step 235), on the second grid, an indication of a difference between the first lens product and the second lens product. As discussed above, the first lens product may have the first lens configuration similar to the second lens configuration of the second lens product, and as such, the first lens product may be included in the second group of lens products. In some embodiments, the lens selection engine 106 may identify the first lens product in the second grid (e.g., the grid 510), and may modify the second grid by highlighting the first lens product in the second grid. For example, the lens selection engine 106 may insert a marker in the area where the first lens product is presented on the second grid. If the first lens product is presented in a box within the second grid, the lens selection engine 106 may increase a thickness of the edges of the box. In some embodiments, the lens selection system may change a background color/pattern of the presentation of the first lens product. As shown in FIG. 5, the lens selection engine 106 has modified the grid 510 by highlighting an area (e.g., a box 514) that presents the first lens product. In this example, the lens selection engine 106 highlighted the box 514 by placing a marker 516 at a corner of the box 514. However, other embodiments of the lens selection engine 106 may choose to highlight the area of the first lens product on the grid 510 differently, as discussed herein.

Similar to the modified first grid, the highlighting of the first lens product in the modified second grid provides an indication of a distance between the first lens product and the second lens product in the modified second grid, thereby indicating a deviation (e.g., a difference) between the first lens product and the second lens product. The indication of the differences between the first lens product and the second lens product (e.g., via the modified first grid, the modified second grid, etc.) may enable the ECP 170 to perform necessary corrective actions before selecting a lens product and implanting the lens product into the patient's eyes. For example, if the differences are larger than a predetermined threshold, the ECP 170 may perform the measurement of the eye parameters again, as the large difference may indicate that there is a problem with the previous measurements. Thus, when it is determined that the difference between the first lens product and the second lens product is larger than the predetermined threshold, the lens selection engine may also perform an action to provide a warning to the ECP 170, for example, by providing an alert on the GUI 300 indicating the large differences between the first lens product and the second lens product. In some embodiments, the difference between the first lens product and the second lens product is sufficiently large that the first lens product is not included in the second group of lens products (and/or the second lens product is not included in the first group of lens products). Thus, the first lens product (or the second lens product) may not be presented in the modified first grid or the second grid. As such, the highlighting of the area that presents the first lens product and/or the second lens product may not provide the indication of the difference. Thus, the lens selection engine 106 may present an alert, such as a pop-up window on the GUI 300 or a flashing icon, and presenting the differences in spherical power and toricity power between the first and second lens product. In some embodiments, the lens selection engine 106 may also transmit an alert to another device (e.g., a mobile device) of the ECP 170 when the difference between the first lens product and the second lens product is larger than the predetermined threshold.

In some embodiments, the selection of the first and second lens products, and/or the selection of the first and second groups of lens products may be performed with the assistance of a machine learning model. For example, the machine learning model may be trained with historical data associated with ECPs selection of the lens products based on biometric data of patients' eyes. As discussed above, it is not uncommon that an ECP would select a lens product for a patient's eye that does not produce the optimal resulting vision based on a variety of factors. As such, by learning what lens products ECPs have selected for patients in the past, the machine learning model may better predict lens products that the ECP would ultimately use for the patient's eye. For example, after performing the IOL surgery, the ECP device 130 may obtain post-operation data (e.g., the eye measurement, vision quality, etc.), for example, from the diagnostic device 160 or through a survey conducted with the patient. The post-operation data can be used in combination with the lenses selected for the patient as training data for training the machine learning model. Details of the machine learning model is described further below by reference to FIG. 7.

Figure 6A:
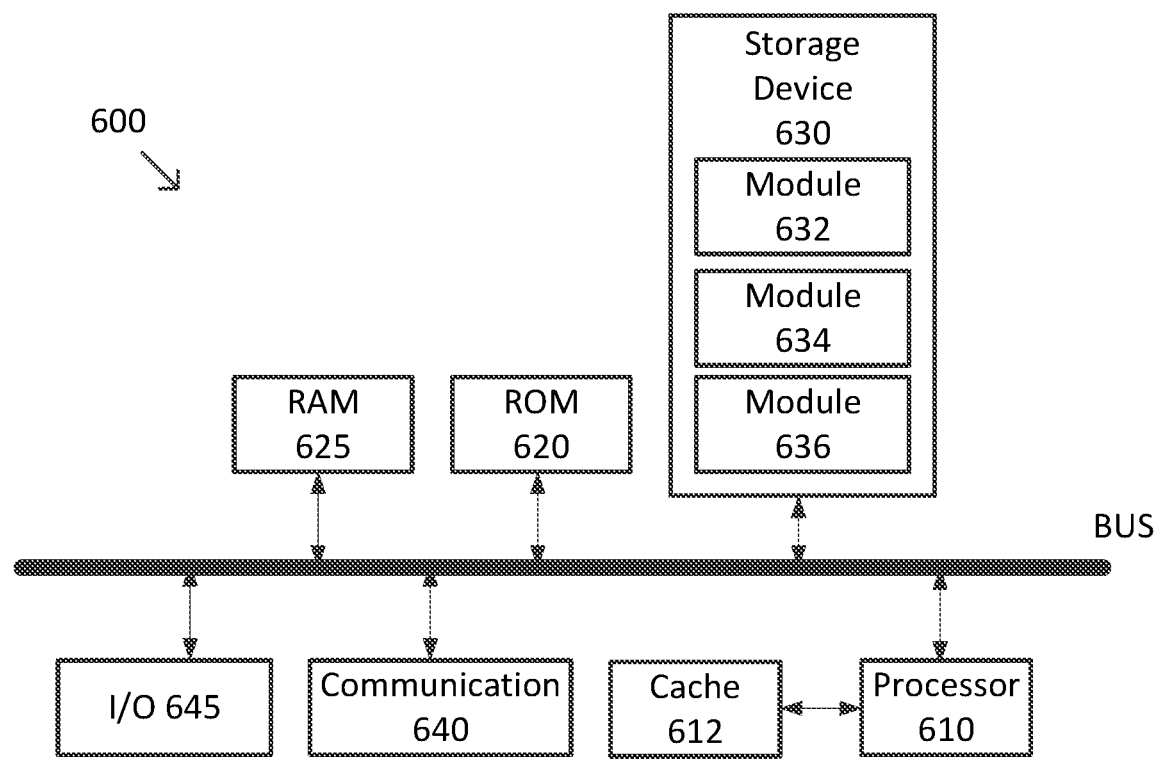
FIGS. 6A and 6B are diagrams of processing systems according to some embodiments.
Figure 6B:
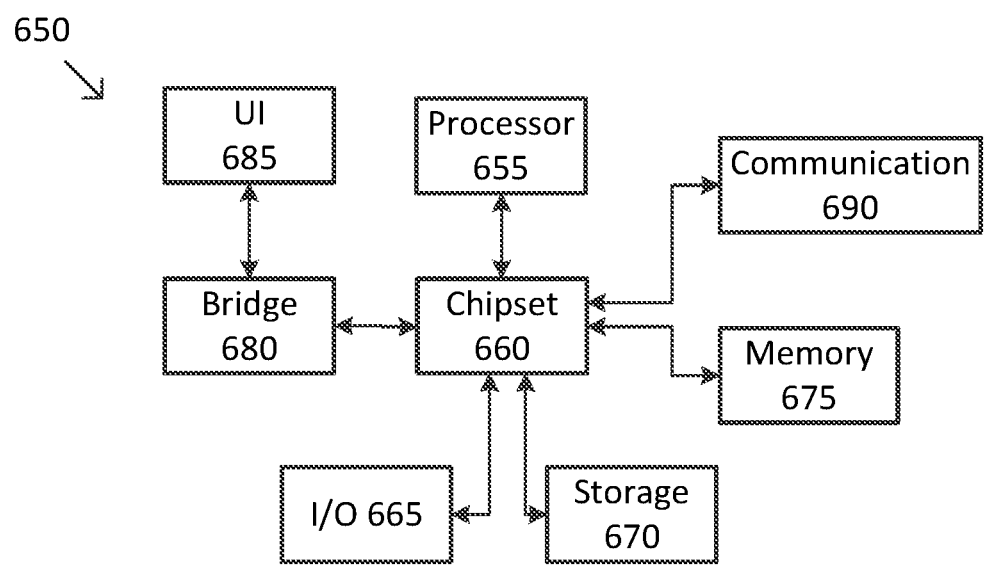

FIGS. 6A and 6B are diagrams of processing systems according to some embodiments. Although two embodiments are shown in FIGS. 6A and 46B, persons of ordinary skill in the art will also readily appreciate that other system embodiments are possible. According to some embodiments, the processing systems of FIGS. 6A and/or 6B are representative of computing systems that may be included in one or more of lens selection platform 102 and the ECP devices 130, 140, and 150, and/or the like.

FIG. 6A illustrates a computing system 600 where the components of system 600 are in electrical communication with each other using a bus 605. System 600 includes a processor 610 and a system bus 605 that couples various system components including memory in the form of a read only memory (ROM) 620, a random access memory (RAM) 625, and/or the like (e.g., PROM, EPROM, FLASH-EPROM, and/or any other memory chip or cartridge) to processor 610. System 600 may further include a cache 612 of high-speed memory connected directly with, in close proximity to, or integrated as part of processor 610. System 600 may access data stored in ROM 620, RAM 625, and/or one or more storage devices 630 through cache 612 for high-speed access by processor 610. In some examples, cache 612 may provide a performance boost that avoids delays by processor 610 in accessing data from memory 615, ROM 620, RAM 625, and/or the one or more storage devices 630 previously stored in cache 612. In some examples, the one or more storage devices 630 store one or more software modules (e.g., software modules 632, 634, 636, and/or the like). Software modules 462, 634, and/or 636 may control and/or be configured to control processor 610 to perform various actions, such as the processes of methods 300 and/or 500. And although system 600 is shown with only one processor 610, it is understood that processor 610 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, system 400 may be implemented as a stand-alone subsystem and/or as a board added to a computing device or as a virtual machine.

To enable user interaction with system 600, system 600 includes one or more communication interfaces 640 and/or one or more input/output (I/O) devices 645. In some examples, the one or more communication interfaces 640 may include one or more network interfaces, network interface cards, and/or the like to provide communication according to one or more network and/or communication bus standards. In some examples, the one or more communication interfaces 440 may include interfaces for communicating with system 600 via a network, such as network 115. In some examples, the one or more I/O devices 645 may include on or more user interface devices (e.g., keyboards, pointing/selection devices (e.g., mice, touch pads, scroll wheels, track balls, touch screens, and/or the like), audio devices (e.g., microphones and/or speakers), sensors, actuators, display devices, and/or the like).

Each of the one or more storage devices 630 may include non-transitory and non-volatile storage such as that provided by a hard disk, an optical medium, a solid-state drive, and/or the like. In some examples, each of the one or more storage devices 630 may be co-located with system 600 (e.g., a local storage device) and/or remote from system 600 (e.g., a cloud storage device).

FIG. 6B illustrates a computing system 650 based on a chipset architecture that may be used in performing any of the methods (e.g., methods 300 and/or 510) described herein. System 650 may include a processor 655, representative of any number of physically and/or logically distinct resources capable of executing software, firmware, and/or other computations, such as one or more CPUs, multi-core processors, microprocessors, microcontrollers, DSPs, FPGAs, ASICs, GPUs, TPUs, and/or the like. As shown, processor 655 is aided by one or more chipsets 660, which may also include one or more CPUs, multi-core processors, microprocessors, microcontrollers, DSPs, FPGAs, ASICs, GPUs, TPUs, co-processors, coder-decoders (CODECs), and/or the like. As shown, the one or more chipsets 660 interface processor 655 with one or more of one or more I/O devices 665, one or more storage devices 670, memory 675, a bridge 680, and/or one or more communication interfaces 690. In some examples, the one or more I/O devices 665, one or more storage devices 670, memory, and/or one or more communication interfaces 690 may correspond to the similarly named counterparts in FIG. 6A and system 600.

In some examples, bridge 680 may provide an additional interface for providing system 650 with access to one or more user interface (UI) components, such as one or more keyboards, pointing/selection devices (e.g., mice, touch pads, scroll wheels, track balls, touch screens, and/or the like), audio devices (e.g., microphones and/or speakers), display devices, and/or the like. According to some embodiments, systems 600 and/or 650 may provide a graphical user interface (GUI) suitable for aiding a user (e.g., a surgeon and/or other medical personnel) in the performance of the processes of method 200.

Methods according to the above-described embodiments may be implemented as executable instructions that are stored on non-transitory, tangible, machine-readable media. The executable instructions, when run by one or more processors (e.g., processor 610 and/or processor 655) may cause the one or more processors to perform one or more of the processes of methods 200 and/or 210. Some common forms of machine-readable media that may include the processes of methods 200 and/or 210 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Figure 7:
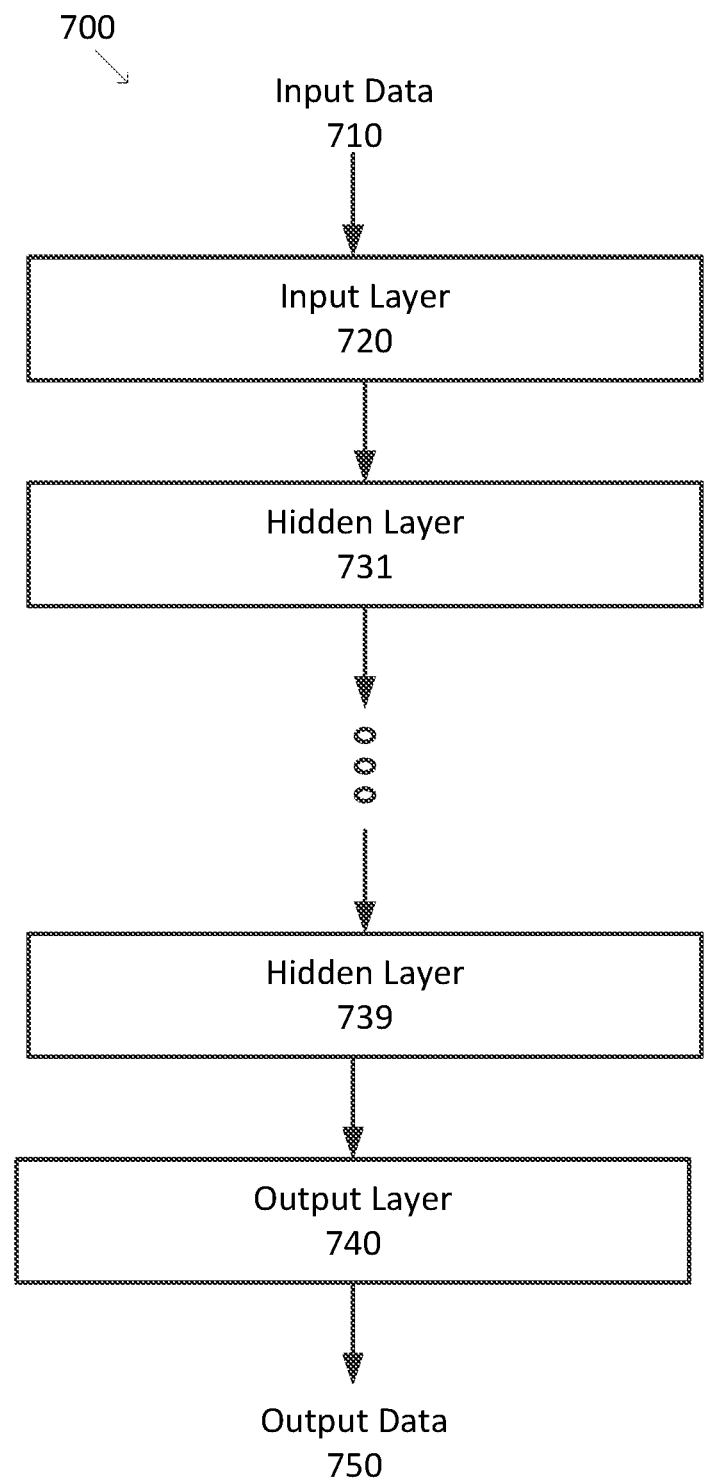
FIG. 7 is a diagram of a multi-layer neural network according to some embodiments.

FIG. 7 is a diagram of a multi-layer neural network 700 according to some embodiments. In some embodiments, neural network 700 may be representative of a neural network used to implement a machine learning model for predicting the first and second lens products and/or the first and second groups of lens products as discussed herein. Neural network 700 processes input data 710 using an input layer 720. In some examples, input data 710 may correspond to the input data provided to the one or more models and/or the training data provided to the one or more models during the training process used to train the one or more models. Input layer 720 includes a plurality of neurons that are used to condition input data 710 by scaling, range limiting, and/or the like. Each of the neurons in input layer 720 generates an output that is fed to the inputs of a hidden layer 731. Hidden layer 731 includes a plurality of neurons that process the outputs from input layer 720. In some examples, each of the neurons in hidden layer 731 generates an output that are then propagated through one or more additional hidden layers that end with hidden layer 739. Hidden layer 739 includes a plurality of neurons that process the outputs from the previous hidden layer. The outputs of hidden layer 739 are fed to an output layer 740. Output layer 740 includes one or more neurons that are used to condition the output from hidden layer 739 by scaling, range limiting, and/or the like. It should be understood that the architecture of neural network 700 is representative only and that other architectures are possible, including a neural network with only one hidden layer, a neural network without an input layer and/or output layer, a neural network with recurrent layers, and/or the like.

In some examples, each of input layer 720, hidden layers 731-739, and/or output layer 740 includes one or more neurons. In some examples, each of input layer 720, hidden layers 731-739, and/or output layer 740 may include a same number or a different number of neurons. In some examples, each of the neurons takes a combination (e.g., a weighted sum using a trainable weighting matrix W) of its inputs x, adds an optional trainable bias b, and applies an activation function f to generate an output a as shown in Equation 1. In some examples, the activation function f may be a linear activation function, an activation function with upper and/or lower limits, a log-sigmoid function, a hyperbolic tangent function, a rectified linear unit function, and/or the like. In some examples, each of the neurons may have a same or a different activation function.

$$a=f(Wx+b) \quad (1)$$

In some examples, neural network 700 may be trained using supervised learning where combinations of training data (e.g., biometric data of patients, etc.) that include a combination of input data and a ground truth (e.g., expected) output data (e.g., lens products selected by ECPs for the patients in the past, etc.). Differences between the output of neural network 700 as generated using the input data for input data 710 and comparing output data 750 as generated by neural network 700 to the ground truth output data. Differences between the generated output data 750 and the ground truth output data may then be fed back into neural network 700 to make corrections to the various trainable weights and biases. In some examples, the differences may be fed back using a back propagation technique using a stochastic gradient descent algorithm, and/or the like. In some examples, a large set of training data combinations may be presented to neural network 700 multiple times until an overall loss function (e.g., a mean-squared error based on the differences of each training combination) converges to an acceptable level.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system, comprising:
a non-transitory memory; and
one or more hardware processors coupled with the non-transitory memory and configured to read instructions from the non-transitory memory to cause the system to perform operations comprising:
obtaining first biometric data associated with an eye of a patient;
determining, from a plurality of lens products, a first set of lens products based on the first biometric data, wherein each lens product in the plurality of lens products corresponds to a particular spherical power and a particular toricity power, and wherein the first set of lens products comprises a first lens product having an associated resulting refraction value for the eye closest to a target refraction value based on the first biometric data;
obtaining second biometric data associated with the eye of the patient after an existing lens of the eye has been removed;
determining, from the plurality of lens products, a second set of lens products based on the second biometric data, wherein the second set of lens products comprises a second lens product having an associated resulting refraction value for the eye closest to the target refraction value based on the second biometric data; and
presenting, on a graphical user interface (GUI) of a device, a grid representing at least the first lens product and the second lens product.

2. The system of claim 1, wherein the grid represents the second set of lens products, and wherein the grid comprises a first dimension corresponding to spherical powers and a second dimension corresponding to toricity powers.

3. The system of claim 2, wherein lens products from the second set of lens products having a same toricity power are arranged along the first dimension of the grid, and wherein lens products from the second set of lens products having a same spherical powers are arranged along the second dimension of the grid.

4. The system of claim 2, wherein the second lens product is presented at a center of the grid.

5. The system of claim 4, wherein each particular lens product of the second set of lens product is arranged on the grid at a distance from the center of the grid based on one or more differences in spherical power and/or toricity power between the particular lens product and the second lens product.

6. The system of claim 1, wherein the operations further comprise:

identifying an area on the grid that presents the first lens product; and highlighting the area of the grid.

7. The system of claim 1, wherein the grid represents the first set of lens products, wherein the first lens product is presented at a center of the grid, and wherein the operations further comprise:

identifying an area on the grid that presents the second lens product; and highlighting the area of the grid.

8. A non-transitory machine-readable medium having stored thereon machine-readable instructions executable to cause a machine to perform operations comprising:

obtaining first biometric data associated with an eye of a patient;

determining, from a plurality of lens products, a first lens product having an associated resulting refraction value for the eye closest to a target refraction value based on the first biometric data;

obtaining second biometric data associated with the eye of the patient after an existing lens of the eye has been removed;

determining, from the plurality of lens products, a second lens product having an associated resulting refraction value for the eye closest to the target refraction value based on the second biometric data; and presenting, on a graphical user interface (GUI) of a device, a grid representing at least the first lens product and the second lens product.

9. The non-transitory machine-readable medium of claim 8, wherein the operations further comprise:

determining, from the plurality of lens products, a set of lens products based on the second biometric data, wherein the grid represents the set of lens products comprising the first lens product and the second lens product.

10. The non-transitory machine-readable medium of claim 9, wherein the second lens product is presented at a center of the grid.

11. The non-transitory machine-readable medium of claim 10, wherein the operations further comprise:

identifying an area on the grid that presents the first lens product; and highlighting the area of the grid.

12. The non-transitory machine-readable medium of claim 8, wherein the operations further comprise:

determining, from the plurality of lens products, a set of lens products based on the first biometric data, wherein the grid represents the set of lens products comprising the first lens product and the second lens product.

13. The non-transitory machine-readable medium of claim 12, wherein the first lens product is presented at a center of the grid, and wherein the operations further comprise:

identifying an area on the grid that presents the second lens product; and highlighting the area of the grid.

* * * * *